| United States Patent [19] | [11] Patent Number: 4,528,207 |
| Johnson | [45] Date of Patent: Jul. 9, 1985 |

[54] PLATED DENTAL AMALGAM ALLOYS

[75] Inventor: Lewis B. Johnson, Charlottesville, Va.

[73] Assignee: The University of Virginia Alumni Patents Foundation, Charlottesville, Va.

[21] Appl. No.: 559,858

[22] Filed: Dec. 12, 1983

Related U.S. Application Data

[63] Continuation of Ser. No. 385,277, Jun. 4, 1982, abandoned.

[51] Int. Cl.$^3$ ............................ C23C 3/00; A61K 5/02
[52] U.S. Cl. ........................................... 427/3; 427/2; 427/216; 427/217; 427/437; 106/1.23
[58] Field of Search ............... 428/570; 427/2, 3, 216, 427/436, 437, 217; 75/169, 173 R; 204/20, 23, 43 R, 43 S; 106/1.23

[56] References Cited

U.S. PATENT DOCUMENTS

| 2,735,788 | 2/1956 | Lowenheim et al. | 427/436 |
| 3,337,350 | 8/1967 | Hata et al. | 427/436 |
| 3,738,920 | 6/1973 | Viglione | 204/43 R |
| 4,046,643 | 9/1977 | Rippere | 204/23 |

FOREIGN PATENT DOCUMENTS

| 2545576 | 4/1976 | Fed. Rep. of Germany | 204/23 |
| 2526544 | 12/1976 | Fed. Rep. of Germany | 75/169 |
| 3018874 | 11/1980 | Fed. Rep. of Germany | 428/570 |
| 53-110929 | 9/1978 | Japan | 204/43 S |

OTHER PUBLICATIONS

Skoog, D. A. et al., *Fundamentals of Analytical Chemistry*, Holt, Rinehart and Winston, Inc., pp. 813–815 (1969).
Leidheiser, H., et al., "Pulse Electroplating of Ag–Sn Alloys and the Formation of Ag$_3$Sn", J. Elec. Chem. Soc., Elec. Science and Tech., pp. 484–487 (1973).
*46th Guidebook Directory for Metal Finishing*, Metal Finishing, pp. 314–315, (1978).

*Primary Examiner*—L. Dewayne Rutledge
*Assistant Examiner*—John J. Zimmerman
*Attorney, Agent, or Firm*—Oblon, Fisher Spivak, McClelland & Maier

[57] ABSTRACT

Dental alloy particles having a coating of a silver-tin alloy are prepared by a process comprising codepositing silver and tin from a cyanide based plating solution containing silver and tin ions on a particulate metal substrate having a particle size sufficient to allow integral bonding between the alloy layer and the particulate substrate.

10 Claims, No Drawings

PLATED DENTAL AMALGAM ALLOYS

This application is a continuation of application Ser. No. 385,277, filed June 4, 1982, now abandoned.

BACKGROUND OF THE INVENTION

1. Field of the Invention

The present invention relates to a dental amalgam alloy for use in dental restorations. More particularly, it relates to a process for manufacturing particles coated with silver-tin alloy for use in the preparation of dental restoration.

2. Description of the Prior Art

Conventional dental amalgam alloys currently in widespread use contain approximately 65 wt % Ag, 20 wt % Sn and 15 wt % Cu with the possible inclusion of minor amounts of other metals including gold for specific purposes. Once these alloys are amalgamated with mercury, the product takes on the appearance of small granules or flakes of whitish gray color. Normally, dental alloys are prepared by melting all or a portion of the metals which constitute the alloy together and then obtaining an ingot which is then machined or ground to a powder. Smaller amounts of other metals can then be mixed with the powdered alloy if desired, and then the resulting powdered alloy is heat treated prior to pelletizing or packaging.

While silver is primarily used as the noble metal in most dental alloys, gold can also be used. However, it is normally not used because of its significantly high cost. An example of a dental alloy containing gold, as shown in U.S. Pat. No. 1,164,997, is one in which an alloy of baser metals including tin, copper, silver, zinc, aluminum and the like is formed. After granulating or flaking the alloy, the individual particles are then provided with a coating or envelope of gold. The gold coated alloy particles can then be amalgamated and used in the normal fashion to complete a dental restoration.

Metal coated alloy or metal particles have been used for different purposes unrelated to dentistry. U.S. Pat. No. 2,294,895 shows an electrolytic powder prepared by coating a thin film of tin on copper particles. The amount of tin utilized ranges from 0.05% to 0.3%. U.S. Pat. No. 2,273,832 shows a similar type of alloy powder in which copper particles are coated with tin, while U.S. Pat. No. 2,286,237 shows the coating of copper particles with such metals as zinc, lead, cadmium and bismuth. U.S. Pat. Nos. 2,018,343 and 3,202,488 show the preparation of electrically conductive metal particles in which particles of a base metal such as copper or zinc are coated with silver. The particles are normally applied to a substrate such as plastic thereby forming an electrically conductive layer on the underlying substrate.

Because of the high percentage of silver in conventional dental alloys and because of the complexity of preparing dental alloys, the cost to the dentist in the purchase of the alloy materials is very high, currently varying between $40 and $100 an ounce. At the current cost levels of silver, considerable savings potentially may be realized if a satisfactory alloy could be manufactured which contains smaller amounts of silver. British Patent Publication No. 2,051,132A discloses a silver containing dental alloy which contains substantially less silver than conventional dental alloys. The reduction in the amount of silver present in the alloy is achieved by coating a particulate core material either free of silver or containing only relatively small amounts of silver such as powdered copper with a layer of conventional silver-tin dental alloy. Since the overall alloy contains substantially less silver than conventional dental alloys, significant savings in the cost of silver can be realized. The powdered alloy is used just as a conventional dental alloy is used in the preparation of a dental amalgam restoration. However, the methods disclosed for preparing the dental alloy powder are relatively complex and are: (1) rumbling, (2) electroplating with an applied current, and (3) electroless plating which requires a reducing agent to supply electrons. Moreover, all of the techniques disclosed in the reference show the deposition of silver and tin as separate layers on the core particles. The reference does not show the simultaneous deposition of silver and tin in a single layer on core particles. A need, therefore, continues to exist for a simpler and cheaper method of preparing dental alloy particles comprising a single layer of silver and tin deposited on a powdered core substrate.

SUMMARY OF THE INVENTION

Accordingly, one object of the present invention is to provide an alloy satisfactory for dental purposes which contains significantly less than the usual amounts of silver thereby lowering the costs of the dental alloy.

Another object of the present invention is to provide a cheaper and simpler method of preparing dental alloy particles wherein the particles are formed of a powdered core substrate coated with a single layer of silver-tin dental alloy.

Briefly, this object and other objects of the present invention as hereinafter will become more readily apparent can be attained by a method of preparing dental alloy particles coated with a single layer of silver-tin alloy by codepositing silver and tin from a cyanide based plating solution containing silver and tin ions on a particulate metal substrate having a particle size sufficient to allow integral bonding between the alloy layer and the particulate substrate.

DESCRIPTION OF THE PREFERRED EMBODIMENTS

In current dental practice, the silver based alloy which is usually employed to complete dental restorations contains about 65% silver, about 20% tin and up to about 15% copper (percentage by weight). The principal alloy in the mixture in Ag$_3$Sn. In order to complete a restoration the dentist mixes a silver alloy powder or pellet with about its weight of mercury and fills the prepared tooth cavity with the resulting plastic mass. The amalgam sets to a usable hardness and strength within several hours. The alloy phases of the set amalgam consist of partially reacted particles of Ag$_3$Sn in a matrix of a silver-mercury phase, Ag$_2$Hg$_3$ and a tin-mercury phase, Sn$_8$Hg.

The silver-tin based alloy from which the amalgam restoration is prepared is very expensive for two basic reasons. First, the alloy contains about 65% by silver by weight, and second, the alloy manufacturing process requires the high temperature melting of the metal constituents of the alloy and the machining, cleaning and heat treating of the alloy. Both of these factors are of considerable present-day concern because the material cost of tooth filling is now a significant portion of the cost to a patient, while about ten years ago, the material cost was almost insignificant.

An important aspect of the present invention is the substitution of a significant portion of the silver-tin mixture of a conventional dental alloy with a baser metal, and therefore cheaper metal, so that when the dental alloy is amalgamated with mercury and sets in a restoration, the particles of the base metal are bonded within the matrix of the two mercury containing alloy phases. In other words, in the present invention a dental alloy is prepared in which particles of a base metal are coated with a silver-tin alloy. The present particulate alloy mass is such that a significant amount of the alloy mass, instead of being the usual silver-tin alloy, is, in fact, a base metal. When the powdered or pelleted alloy is amalgamated with mercury, the resulting restoration will consist of discrete particles of the base metal dispersed throughout the alloy phases of the restoration. This structure is different from restorations made from conventional dental alloys which contain comparatively lesser quantities of a base metal such as copper in that the resulting restoration does not contain particles of a base metal dispersed throughout the alloy matrix of the restoration. Because significant quantities of silver are eliminated in the production of dental alloys, the cost of silver based dental alloy can be reduced.

The central feature of the present invention is the provision of a process for manufacturing coated dental alloy particles which is simpler and cheaper than prior art techniques for preparing such particles. The present invention therefore represents a further advance in the art for providing a dental alloy at reduced costs as a raw material for the preparation of dental amalgam restorations. In the method of the present invention a particulate base metal is coated with a single layer of silver-tin alloy in an aqueous cyanide ion containing bath. The particulate base material can be any base metal or alloy which integrally bonds with the applied silver-tin layer. The particulate base metal should contain less than 20% by wt silver, and preferably less than 10% by wt silver. In fact, the particulate base metal most preferably is free of silver. The particulate base metal may be of such metals as copper as well as copper alloys such as copper-manganese alloys. Other base metals include such non-amalgamable metals as Co, Ti, Cr, V, Nb, Mo, Mn and Ta. The particles of base metal may be solid or hollow and may be of any convenient shape such as spherical, semispherical or flake-like. The particulate base metal should be of a size such that the covering silver-tin layer, in fact, codeposits integrally and strongly bonds to the base metal particles. The particles normally range in size from 1 to 10 $\mu$m, preferably 1-5 $\mu$m in diameter or cross-sectional distance.

In the coating step of the present process silver and tin are simultaneously codeposited from solution onto the base metal particles. Codeposition of silver and tin is conducted from a cyanide ion containing bath where the cyanide ion concentration is such that the Ag and Sn ions are stabilized as complex cyanide ions in solution. Any convenient source of cyanide ion can be used such as an alkali metal or alkaline earth metal cyanide. Silver cyanide can also be a source of cyanide ion. An important feature of the present process is the finding that both silver and tin will deposit from a cyanide solution in a single layer without the application of current or a reducing agent. In other words, silver and tin codeposit from solution by virtue of their electrochemical potentials. Normally, silver and tin should be present in the cyanide solution in concentrations such that the amount of silver plated on the particulate metal substrate is no more than 10 wt % while the amount of tin plated is about 5-6 wt %, said percentages based on the total weight of coated particles. A factor which controls silver ion and tin ion concentration in the bath is that the silver and tin which deposits should be present in the alloy layer in amounts accepted for a dental alloy.

Suitable sources of tin ion include such water soluble salts as $K_2SnO_3$. Tin halides cannot be used since the presence of halide ion in solution would result in the precipitation of silver as a halide salt from solution. Suitable water soluble silver salts which can be codissolved with the tin salt include silver cyanide.

The temperature of the codeposition bath is not critical. However, for practical reasons a temperature ranging from 20° C. to 24° C. (room temperature), preferably 22° C., is appropriate.

The codeposition process of the present invention should be conducted at a pH which is not acidic in view of the presence of cyanide ion in solution which would be volatilized as toxic HCN from acidic solutions. For safety reasons the aqueous deposition solutions should be basic, preferably at a pH of about 10–12.

The coated particulate product of the present invention is composed of about 80 wt % or less of the base metal particles and about 20 wt % or more of silver-tin alloy. The product obtained must be of a particle size which is suitable for the preparation of a dental amalgam, and generally is of a size which passes a 400 mesh screen.

The particulate dental alloy of the present invention looks like a conventional dental alloy and can be worked just like a conventional alloy.

Having generally described this invention, a further understanding can be obtained by reference to certain specific examples which are provided herein for purposes of illustration only and are not intended to be limiting unless otherwise specified.

In a 1000 ml glass beaker containing 200 ml of distilled water is dissolved 24 g KCN and 1.5 g KOH. These amounts are equivalent to 120 g/liter or about a 1.8 N solution of KCN and 7.5 g/liter or 0.13 N solution of KOH. A solution having the indicated hydroxide ion concentration has a pH of above 12. The high pH being necessary to avoid the evolution of gaseous HCN and because the plating of metal from solution is better and more efficient at high pH values.

In a second 1000 ml beaker containing 200 ml of distilled water is dissolved 24 g KCN, 1.5 g KOH and an amount of AgCN depending on the amount of copper powder to be plated and the extent to which the powder is plated, which in this case is 10 g Cu powder, to have an alloy coating such that the coated product contains 10 wt % Ag. The amount of AgCN dissolved is about 1.4 g. In this solution is also dissolved about 1.5 g of $K_2SnO_3$ ($K_2SnO_3.3H_2O$) which is an amount sufficient to provide an alloy product containing from 5 to 6 wt % Sn. The amount of $K_2SnO_3$ dissolved in solution depends on the same reasons presented above concerning the amount of AgCN dissolved in solution. The temperature of both solutions is brought to 22° C.

With continuous stirring, 10 g of electrolytic copper dust having a particle size of 1 to 25 $\mu$m in diameter is added to the beaker containing the basic cyanide solution. The particles are slurried for about one minute in the solution in order to completely dissolve any residual oxide material on the surface of the particles. The contents of the beaker containing the Ag and Sn ion solution are then poured rapidly into the slurry and the resulting slurry is stirred strongly for about 30 minutes. The stirring is necessary to obtain even plating of the alloy layer and to minimize agglomeration of the dust.

When the stirring is stopped, the plated dust settles rapidly into somewhat agglomerated masses. The liquid phase is decanted and the solid mass is washed with about 500 ml of distilled water for about 10 minutes, allowed to settle and the wash water decanted. The washing process is repeated as many times as is necessary, usually four to five times. On about the third washing it was observed that the agglomerates begin to break-up into a fine powder which can be suction filtered. After drying at slightly above room temperature, the plated powder is sieved through a 400 mesh standard screen. In most cases all of the plated material will pass through a 400 mesh screen.

A 0.4 g amount of the plated powder was triturated for 30 seconds with 0.6 g of Hg thereby forming a plastic mass which resembles conventional amalgam alloys. The amalgam handled well and packed readily into a dental cavity readily conforming to its shape. After compression the final amalgam contained abut 60 % by wt Hg, exhibited a 24-hour compressive strength of 40–50,000 psi and a creep of about 0.02%. The dimensional change during setting of the restoration was about 0.2%.

Having now fully described the invention, it will be apparent to one of ordinary skill in the art that many changes and modifications can be made thereto without departing from the spirit or scope of the invention as set forth herein.

What is claimed as new and is intended to be secured by Letters Patent is:

1. A method of preparing dental alloy particles coated with a silver-tin alloy, comprising: codepositing silver and tin from a cyanide based plating solution containing silver and tin ions on a particulate metal substrate having a particle size sufficient to allow integral bonding between the alloy layer and the particulate substrate, said codeposition upon the metal substrate occurring by virtue of the electrochemical potentials of said silver and tin ions in solution and not by the application of a current to the solution.

2. The method of claim 1, wherein the cyanide ion concentration in said solution is sufficient to stabilize Ag and Sn ions in solution as complex cyanide ions.

3. The method of claim 1, wherein the silver ion concentration in said solution is sufficient to yield a plated particulate product having a silver content of no more than 10 wt %.

4. the method of claim 1, wherein the tin ion concentration in said solution is sufficient to yield a plated particulate product having a tin content of 5–6 wt %.

5. The method of claim 1, wherein the particulate metal substrate is copper, cobalt, tungsten, vanadium, chromium, niobium, molybdenum, tantalum or titanium or a copper alloy.

6. The method of claim 5, wherein said copper alloy is a copper-manganese alloy.

7. The method of claim 1, wherein said particulate metal substrate is of a particle size ranging from 1–10 $\mu$m.

8. The method of claim 7, wherein said particle size is 1–5 $\mu$m.

9. The method of claim 1, wherein said silver and tin are deposited from solution at a temperature of 20° to 24° C.

10. The method of claim 1, wherein said codeposition process is conducted at a basic pH.

* * * * *